US012417246B2

(12) United States Patent
Kannan et al.

(10) Patent No.: US 12,417,246 B2
(45) Date of Patent: Sep. 16, 2025

(54) KNOWLEDGE GRAPH ANALYTICS KERNELS IN HIGH PERFORMANCE COMPUTING

(71) Applicant: UT-Battelle, LLC, Oak Ridge, TN (US)

(72) Inventors: Ramakrishnan Kannan, Oak Ridge, TN (US); Piyush K. Sao, Oak Ridge, TN (US); Hao Lu, Oak Ridge, TN (US); Drahomira Herrmannova, Oak Ridge, TN (US); Vijay Thakkar, Oak Ridge, TN (US); Robert M. Patton, Oak Ridge, TN (US); Richard W. Vuduc, Oak Ridge, TN (US); Thomas E. Potok, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 952 days.

(21) Appl. No.: 17/389,862

(22) Filed: Jul. 30, 2021

(65) Prior Publication Data
US 2022/0035832 A1 Feb. 3, 2022

Related U.S. Application Data

(60) Provisional application No. 63/059,496, filed on Jul. 31, 2020.

(51) Int. Cl.
*G06F 16/901* (2019.01)
*G06F 16/26* (2019.01)
(Continued)

(52) U.S. Cl.
CPC .......... *G06F 16/9024* (2019.01); *G06F 16/26* (2019.01); *G06N 7/01* (2023.01);
(Continued)

(58) Field of Classification Search
CPC ................ G06F 16/9024; G06F 16/26; G06F 16/24578; G16H 50/70; G16H 70/60; G06N 7/01
See application file for complete search history.

(56) References Cited

U.S. PATENT DOCUMENTS

| 11,640,540 B2* | 5/2023 | Fadnis | G06N 3/04 706/20 |
| 2020/0004873 A1* | 1/2020 | Chang | G06F 16/31 |

(Continued)

OTHER PUBLICATIONS

Zhao et al., "Graphene: A Precise Biomedical Literature Retrieval Engine with Graph Augmented Deep Learning and External Knowledge Empowerment" Nov. 20, 2019, arXiv: 1911.00760v2, pp. 1-10. (Year: 2019).*

(Continued)

*Primary Examiner* — Miranda M Huang
*Assistant Examiner* — Chase P. Hinckley
(74) *Attorney, Agent, or Firm* — Warner Norcross + Judd LLP

(57) ABSTRACT

Data mining large-scale corpora of scholarly publications, such as the full biomedical literature, which may consist of tens of millions of papers spanning decades of research. The present disclosure provides a Distributed Accelerated Semiring All-Pairs Shortest Path (DSNAPSHOT) algorithm for computing shortest paths of a knowledge graph using distributed-memory parallel computers accelerated by GPUs. DSNAPSHOT implementations can analyze connected input graphs with millions of vertices using a large number graphics processing units (e.g., the 24,576 GPUs of the Oak Ridge National Laboratory's Summit supercomputer system). DSNAPSHOT provides sustained performance of about $136*10^{15}$ floating-point operations per second (136 petaflop/s) at a parallel efficiency of about 90% under weak scaling and, in absolute speed, 70% of the performance (Continued)

given our computation (in the single-precision tropical semiring or "min-plus" algebra). DSNAPSHOT may enable mining of scholarly knowledge corpora when embedded and integrated into artificial intelligence-driven natural language processing workflows at scale.

6 Claims, 7 Drawing Sheets

(51) Int. Cl.
  *G06N 7/01* (2023.01)
  *G16H 50/70* (2018.01)
  *G16H 70/60* (2018.01)
  *G06F 16/2457* (2019.01)

(52) U.S. Cl.
  CPC ............. *G16H 50/70* (2018.01); *G16H 70/60* (2018.01); *G06F 16/24578* (2019.01)

(56) References Cited

U.S. PATENT DOCUMENTS

| | | | | |
|---|---|---|---|---|
| 2020/0074301 | A1* | 3/2020 | Shang | G06N 5/02 |
| 2020/0167347 | A1* | 5/2020 | Yu | G06F 16/9024 |
| 2022/0019905 | A1* | 1/2022 | Meyerzon | G06N 3/045 |
| 2022/0035832 | A1* | 2/2022 | Kannan | G16H 70/60 |

OTHER PUBLICATIONS

Alghamdi et al., "Developing the Parallelization Methods for Finding the All-Pairs Shortest Paths in Distributed Memory Architecture" Jan. 16, 2020, pp. 1-8. (Year: 2020).*

Wang et al., "Entity Context and Relational Paths for Knowledge Graph Completion" Feb. 17, 2020, arXiv: 2002.06757v1, pp. 1-12. (Year: 2020).*

Choudhury et al., "Mining Temporal Evolution of Knowledge Graphs and Genealogical Features for Literature-Based Discovery Prediction" Nov. 11, 2019, arXiv: 1907.09395v2, pp. 1-22. (Year: 2019).*

Solomonik et al., "Mining communication in all-pairs shortest paths" 2013, pp. 548-559. (Year: 2013).*

Lin et al., "KagNet: Knowledge-Aware Graph Networks for Commonsense Reasoning" Sep. 4, 2019, arXiv: 1909.0215v1, pp. 1-11. (Year: 2019).*

Matsumoto et al., "Blocked United Algorithm for the All-Pairs Shortest Paths Problem on Hybrid CPU-GPU Systems" Dec. 2012, pp. 2759-2768. (Year: 2012).*

Mishra "Utilization of OpenCL for Large Graph Problems on Graphics Processing Unit" 2017, pp. 125-135. (Year: 2017).*

Djidjev et al., "All-Pairs Shortest Path algorithms for planar graph for GPU-accelerated clusters" Jul. 2015, pp. 91-103. (Year: 2015).*

Elekes et Szarnyas, "An incremental GraphBLAS solution for the 2018 TTC Social Media case study" Jul. 28, 2020, pp. 203-206. (Year: 2020).*

Ben-Nun et al., "Groute: Asynchronous Multi-GPU Programming Model with Applications to Large-scale Graph Processing" Jun. 2020, pp. 1-27. (Year: 2020).*

Agarwal et Ramachandran, "Faster Deterministic All Pairs Shortest Path in Congest Model" Jul. 2020, pp. 11-21. (Year: 2020).*

Bringmann et al., "Aproximating APSP without Scaling: Equivalence of Approximate Min-Plus and Exact Min-Max" Jul. 25, 2019, arXiv: 1907.11078v1, pp. 1-34. (Year: 2019).*

Chen et al., "Coronavirus Knowledge Graph: A Case Study" Jul. 4, 2020, arXiv: 2007.10287v1, pp. 1-8. (Year: 2020).*

Nakao et al., "Parallelization of All-Pairs-Shortest-Path Algorithms in Unweighted Graph" Jan. 2020, pp. 1-10. (Year: 2020).*

Terekhov et al., "Context-Free Path Querying with Single-Path Semantics by Matrix Multiplication" Jun. 2020, pp. 1-12. (Year: 2020).*

Swanson, D.R. et al., "An interactive system for finding complementary literatures: a stimulus to scientific discovery", Artificial Intelligence, vol. 91, No. 2, Apr. 1997, pp. 183-203.

Tshitoyan, V. et al., "Unsupervised word embeddings capture latent knowledge from materials science literature", Nature, vol. 571, No. 7763, Jul. 2019, pp. 95-98.

Stegmann, J. et al., "Hypothesis generation guided by co-word clustering", Scientometrics, vol. 56, No. 1, 2003, pp. 111-135.

Solomonik, E. et al., "Minimizing communication in all-pairs shortest paths", in Proceedings of the 27th IEEE International Parallel and Distributed Processing Symposium, Boston, MA, 2013, pp. 1-13.

Sybrandt, J. et al., "Moliere: Automatic biomedical hypothesis generation system", in Proceedings of the 23rd ACM SIGKDD International Conference on Knowledge Discovery and Data Mining, 2017, pp. 1633-1642.

Thilakaratne, M. et al., "A systematic review on literature-based discovery: General overview, methodology, & statistical analysis", ACM Computing Surveys, vol. 52, No. 6, 2019, pp. 1-34.

Baek, S.H. et al., "Enriching plausible new hypothesis generation in pubmed", PloS one, vol. 12, No. 7, 2017, pp. 1-18.

Sao, P. et al., "A supernodal all-pairs shortest path algorithm", Principles and Practice of Parallel Programming, 2020, pp. 1-12.

Fineman, J.T. et al, "Fundamental graph algorithms", Graph Algorithms in the Language of Linear Algebra, Society of Industrial and Applied Mathematics, 2011, Chapter 5, pp. 45-58.

\* cited by examiner

KNOWLEDGE GRAPH ANALYTICS KERNELS IN HIGH PERFORMANCE COMPUTING

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

BACKGROUND OF THE INVENTION

The amount of scientific literature is expanding at an incredible rate, which has been estimated to be in the millions of new articles per year and growing exponentially. Efficiently extracting information from such vast stores of knowledge is an urgent need in a variety of different research areas. This expanding volume of information to parse for such endeavors is beyond the capacity of any one person. Accordingly, there is a strong motivation to develop computer-based automated knowledge-mining methods and extraction tools.

One common method of knowledge mining is via literature-based discovery ("LBD"). Literature-based discovery is a form of knowledge extraction and automated hypothesis generation that uses papers and other academic publications to find new relationships between existing knowledge. Typically, to aid in the discovery, the literature is organized into a knowledge graph. Knowledge graph construction involves the acquisition and integration of information into an ontology from which the new information can be uncovered or discovered. That is, previously unknown relationships that exist in scientific literature can be uncovered by identifying concepts that link disconnected entities in the knowledge graph. This process is generally referred to as Swanson linking and is based on the familiar idea of transitivity where if there is no known direct relation between entities A and C, but there are published relations between A and B, and B and C, then it is reasonable to hypothesize that there is a plausible, novel, yet unpublished indirect relation between A and C. For instance, in 1986, Don Swanson applied this concept to propose a connection between dietary fish oil and Raynaud's disease through high blood viscosity, which fish oil reduces. This connection was validated in a clinical trial three years later.

A general graphical representation useful in understanding several LBD approaches is illustrated in FIG. 1. Literature based discovery generally begins with one or a set of starting document(s)/concept(s). Some LBD methods include: co-occurrence methods, relation-mining methods, and embedding methods. These methods have a number of shortcomings:

- Limited to providing results for a specific query-requires significant prior expertise
- Co-occurrence methods are typically low precision-high recall (retrieve lots of false positives, introduce noise)
- Relation-mining methods are typically higher precision but low recall (result in false negatives, can miss important connections)
- Embedding-based similarity methods are black-box methods that require additional work to provide an explanation for connection.

There is a need for efficient knowledge mining algorithms and software, especially at scale. To aid in explanation, the present disclosure refers to Semantic MEDLINE, a knowledge graph dataset of biomedical concepts and relations between them extracted from the PubMed database of biomedical literature maintained by the U.S. National Library of Medicine. This knowledge graph dataset was enriched with data extracted from research literature on COVID-19, SARS-COV-2, and other coronaviruses. The graph dataset consists of 18.5 million vertices representing over 290 thousand unique biomedical concepts and the publication abstracts from which these concepts were extracted. The roughly 213 million relations between these vertices represent 1) existing published relations between biomedical concepts, 2) relations between concepts and publication abstracts in which they appear, and 3) citation relations between the abstracts.

The analysis of this and other similar datasets presents several challenges. The knowledge graph is not only extremely large but is also constantly growing. For example, adding research articles on COVID-19 published over a short period of time would enlarge the graph by several thousand vertices and add tens of thousands of new edges. Accordingly, in order to aid in the analysis of such a large graph, an enterprise architecture for biomedical knowledge graph analytics is needed. A high performance computing (HPC) environment can generally be leveraged to address some of the challenges. However, there is ample room for improvement with the various systems and methods associated with conducting efficient and effective computer-based automated knowledge mining.

By way of example, in the biomedical field, the relations between biomedical concepts—such as drugs, diseases, symptoms, proteins, and genes—play an important role in tasks like drug discovery and repurposing. Much previous work has focused on leveraging natural language models for speeding up these tasks. However, these methods are often black boxes that involve significant additional work to provide an explanation. Furthermore, these methods are often limited to providing results for a specific query (for example, a specific drug and a disease), significantly limiting their scope and increasing the work and background knowledge to properly utilize them.

Many different approaches have been applied with the goal of performing automated hypothesis generation and literature-based discovery, such as statistical methods and pattern matching, link prediction, association rule mining, manually constructed queries, and graph statistics. Others have explored using shortest-path computations for discovering novel connections between biomedical concepts. These approaches generally use a shortest path calculation to discover pathways between pairs of entities in the knowledge graph that do not otherwise have a direct connection between them. However, these approaches need a starting query (a pair of entities); or need to reduce the size of the graph to specific types of nodes and connections or to specific topics in order to be viable.

Some computer-based knowledge mining systems and methods leverage an all pair shortest path ("APSP") algorithm in order to remove reliance on a starting set of document(s)/concept(s). In addition to removing the reliance on the starting documents, APSP approaches have a number of additional advantages, perhaps the main advantage being the ability to utilize the entire knowledge graph to mine interesting relationships. That is, an APSP algorithm can simultaneously leverage co-occurrences between concepts and relations between concepts. In general, APSP approaches allow a combination of imperfect classifiers to improve overall performance of the algorithm.

Many path problems in graph analysis can be described succinctly with semiring algebra. This formalism and the resulting classical and blocked Floyd-Warshall algorithms for APSP are worth considering within the context of knowledge graph mining and therefore are briefly discussed by way of background.

In order to aid explanation, some information about various knowledge mining nomenclature and notation is provided. An undirected weighted input graph G can be represented by G={V, E, W}, where the graph has a vertex set V containing n=|V| vertices or nodes, an edge set E with m=|E| edges, and associated weights W. The input graph G is typically a single connected component, i.e., there can exist a path of one or more edges between any pair of two vertices $v_i$ and $v_j$ resulting in a fully dense Dist matrix. Further, edge $e_{i,j}$ represents the edge between the $i^{th}$ vertex $v_i$ and the $j^{th}$ vertex $v_j$. The weights are represented by W, a sparse symmetric matrix. A particular weight $w_{i,j}$ denotes the distance between vertices $v_i$ and $v_j$ if those two vertices are directly connected by the $e_{i,j} \in E$. Otherwise, if the two vertices are not connected, then there is essentially an infinite amount of distance between the two vertices (i.e., $w_{i,j}=\infty$). Table I below includes some of this and other relevant notation utilized throughout the disclosure.

TABLE I

| Category | Symbol | Description |
| --- | --- | --- |
| Processes | P | Number of MPI Processes |
|  | $P_x$, $P_y$ | Row and Column Processes |
|  | $P_x(k)$ | (k mod $P_x$)th Process Row |
|  | $P_y(k)$ | (k mod $P_y$)th Process Column |
| Matrices | A | Adjacency matrix of the Graph |
|  | A(:, k) | A(k:n, k) |
|  | A(k, :) | A(k, k + 1:n): kth A panels |
| Graphs | G | Input Graph as in FIG. 5 |
|  | V | Vertex set |
|  | E | Edge set |
|  | n | Number of vertices |
|  | m | Number of edges |

One well-known all-pairs shortest path algorithm is the Floyd-Warshall ("FW") algorithm. In its original form, the FW algorithm finds the shortest paths in a directed weighted graph with positive or negative edge weights (but with no negative cycles). A single execution of the algorithm will find the lengths (summed weights) of shortest paths between all pairs of vertices. Pseudocode for a FW algorithm that identifies all-pairs shortest path is provided in Table II and will now be briefly described.

TABLE II

Algorithm 1 FW algorithm for APSP 1. function FLOYDWARSHALL(G=(V,E)):
2.     Let n←dim(V)
3.     Let Dist$\begin{cases} W_{i,j} & \text{if}(i,j) \in E \\ \infty & \text{otherwise} \end{cases}$ [i, j] =
4.     for k = {1, 2 ...., n} do:
5.       for i = {1, 2..., n} do:
6.         for j = {1, 2..., n} do:
7.           Dist[i,j] = min {Dist[i,j], Dist[i,k]+Dist[k,j]}
8.     Return Dist In essence, the FW algorithm form Table II maintains and updates a 2-D array of distances, Dist[i,j]. At any $k^{th}$ iteration, the FW algorithm maintains the invariance that Dist[i, j] holds the current shortest distance between $v_i$ and $v_j$ with all intermediate vertices $k \in (v_1, v_2, \ldots, v_k)$ so far. This can be represented by the following update equation in the FW algorithm:

$$\text{Dist}^k[i,j] \leftarrow \min\{\text{Dist}^{k-1}[i,j], \text{Dist}^{k-1}[i,k]+\text{Dist}^{k-1}[k,j]\}$$

The above invariance is satisfied when there are no cycles of negative weight sum. In the case of cycles with negative weight sum, the shortest path length is—meaningless and it will be negative infinity $-\infty$. Once all paths are explored between any two pairs of vertices $v_i$ to $v_j$ with all the vertices as intermediaries—that is $\forall k \in V$; then, the distance array, Dist[i,j], will represent the APSP for the entire graph, G. This computation can be done in-place, such that two separate copies of the distance array (e.g., $\text{Dist}^{k-1}$ and $\text{Dist}^k$) are unnecessary, as evidenced by the exemplary FW algorithm pseudocode of Table II.

All-pairs shortest path algorithms can be described algebraically as computing the matrix closure of the weight matrix, W, defined over the tropical semiring, i.e., a semiring of extended real numbers with the operations of minimum or maximum and addition replacing the classical operations of addition and multiplication, respectively. A min tropical semiring (also referred to as Min-Plus semiring) can be represented by the semiring $(R \cup \{+\infty\}, \oplus, \otimes)$.

In a tropical semiring, the symbols $\oplus$, $\otimes$ represent the following two binary scalar operators:

$$x \oplus y := \min(x,y)$$

$$x \perp y == x+y$$

where x and y are real values or infinity $\infty$.

Considering the following two real number matrices:

$$A \in R^{m \times k}$$

$$B \in R^{k \times n}$$

In this scenario, the Min-Plus product C of matrix A and matrix B can be represented as:

$$C_{ij} \leftarrow \sum_k^\oplus A_{ik} \otimes B_{kj} = \min_k(A_{ik} + B_{kj}). \qquad (1)$$

This Min-Plus product C of the A and B matrices highlights the connections between the semiring general matrix multiplication (GEMM) and the APSP.

There are numerous challenges with practical implementation of APSP algorithms, especially within high power computing ("HPC") environments. For example, distributing calculations across multiple processors is non-trivial and brings with it a host of additional challenges. While some attempts have been made with respect to a distributed FW algorithm on a central processing unit and to perform semiring matrix multiplication on a central processing unit, there is ample room for improvement with respect to efficiency, speed, and overall effectiveness of APSP knowledge mining, especially within the context of high performance computer (HPC) environments.

SUMMARY OF THE INVENTION

The present disclosure is generally directed to an enterprise computer architecture for knowledge graph analytics. The enterprise computer architecture incorporates (a) streaming publication data from different sources and the knowledge graph representation of these sources; (b) various client services like natural language processing and visualization; and (c) a backend query engine for operating on the knowledge graph, which can invoke operations such as All-Pairs Shortest Path (APSP).

One aspect of the present disclosure is generally directed to a scalable, distributed, accelerated, semiring all-pairs shortest path (APSP) algorithm (DSNAPSHOT). DSNAPSHOT implements a GPU-accelerated, distributed-memory parallel version of the Floyd-Warshall (FW) algorithm. DSNAPSHOT is the capable of calculating shortest path between all pairs of entities in a biomedical knowledge graph, thereby enabling the discovery of meaningful relations across the whole of biomedical knowledge.

One aspect of the present disclosure is generally directed to a distributed FW algorithm using semiring on a graphics processing unit cluster. This approach provides the ability to analyze and mine larger knowledge graphs than other approaches.

Another aspect of the present disclosure is generally directed to performing semiring on a graphics processing unit. This configuration provides a faster approach than execution of such algorithms on a central processing unit.

In yet another aspect of the present disclosure, a CPU-GPU overlapping based APSP algorithm is provided. The overlapping architecture provides a flexible APSP algorithm that can be performed exclusively on a CPU, exclusively on a GPU, or on a combination of both a CPU and a GPU.

In exclusive GPU embodiments, GPU based communicators can be utilized. Such communicators can be configured to reduce communication burden by placing communicating subprocesses on physically closer machines, which can provide an appreciable speed benefit.

Another aspect of the present disclosure relates to a constrained all pairs shortest path approach which can improve the quality of the results by eliminating unnecessary paths in the resultant knowledge graph.

Another aspect of the present disclosure relates to determining shortest paths between all pairs of nodes of a knowledge graph by processing the matrix with the computing system, wherein the processing is distributed across multiple processors coordinated by a message processing interface that coordinates parallel diagonal updates, panel updates, and min-plus outer products. In some embodiments, the mining can leverage one or a combination of a lookahead technique, bandwidth optimal asynchronous ring communication for broadcast, and assigning a subset of communicating processes to hardware processors at least in part based on physical distance between the hardware processors.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

DESCRIPTION OF THE CURRENT EMBODIMENT

Figure 1:
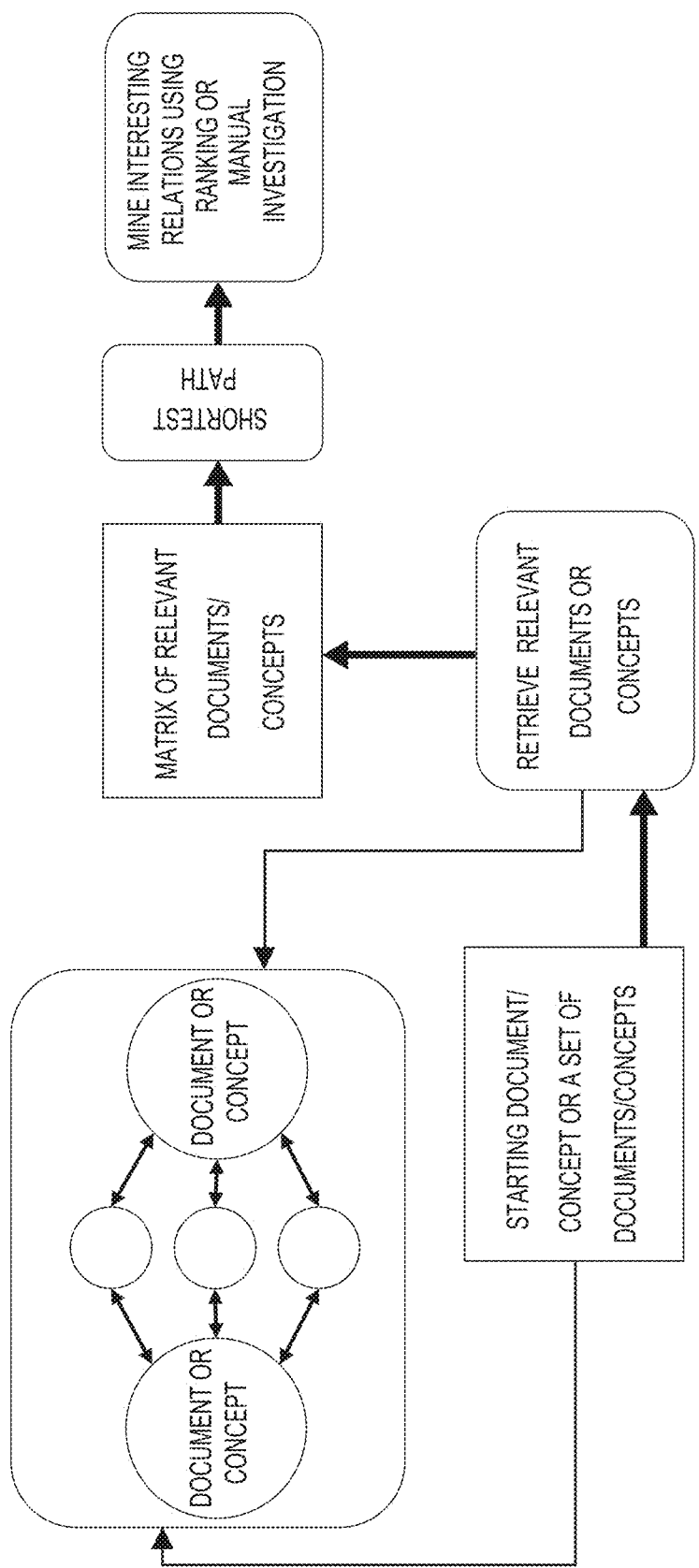
FIG. 1 shows a graphical representation of literature based discovery methods.

One aspect of the present disclosure is generally directed to a distributed accelerated semiring all-pairs shortest path (DSNAPSHOT) algorithm. DSNAPSHOT implements a GPU-accelerated, distributed-memory parallel version of the Floyd-Warshall (FW) algorithm. In one embodiment, DSNAPSHOT can be used calculate the shortest path between all pairs of entities in a knowledge graph, such as a biomedical knowledge graph thereby enabling the discovery of meaningful relations across biomedical knowledge.

Embodiments of DSNAPSHOT, provide a parallel APSP algorithm designed as a diagonal, panel and min-plus outer product that can leverage the following features: lookahead, bandwidth asynchronous ring communication for broadcast, and rank placement. The lookahead feature refers to performing computation and communication concurrently or overlapping. Improved rank placement can be provided by placing the subset of communicating processes closer to each other in physical machines. It is computationally expensive to scale all-pairs shortest path algorithms with tens of millions of vertices on tens of thousands of GPUs. Accordingly, improvements in these algorithms, such as the improvements of DSNAPSHOT, provide an appreciable benefit.

Knowledge mining algorithms can be distributed over a series of processors in order to process the algorithm in parallel and speed up execution time. However, there are significant challenges to doing so because of dependencies and other issues. In essence, in DSNAPSHOT, any step in the algorithm is executed by considering the portion of the input graph and the coordinate of the process in the logical message passing interface ("MPI") process arrangement.

Several "if" conditions verify these two states in order to execute the appropriate sections of the parallel algorithm.

The DSNAPSHOT algorithm can be implemented in a high performance computing (HPC) environment, such as on a supercomputer. For example, the DSNAPSHOT algorithm can be configured and executed on the Summit supercomputer system located at Oak Ridge National Laboratory. DSNAPSHOT is essentially suitable for implementation on a supercomputing system where every networked computer has both CPUs and Graphical processing units that can communicate and coordinate their actions using Message Passing Interface (MPI). DSNAPSHOT is capable of achieving over 100 quadrillion ($10^{15}$) floating-point operations per second, i.e., 100 PFLOPS which is approximately 70% of peak efficiency on Supercomputers with accelerators such as Summit. The other such systems in the world include government owned PizDaint, Fugaku, Sunway Taihulight, and other enterprise supercomputers that can be privately owned on corporations such as Nvidia Selene.

The details of DSNAPSHOT will be discussed in more detail throughout the disclosure, but suffice it to say that at the heart of the DSNAPSHOT algorithm lies matrix-multiplication-like (level-3 basic linear algebra subprograms ("BLAS")-like) operations, which are well-suited to graphics processing units ("GPUs") and distributed memory systems.

Figure 2:
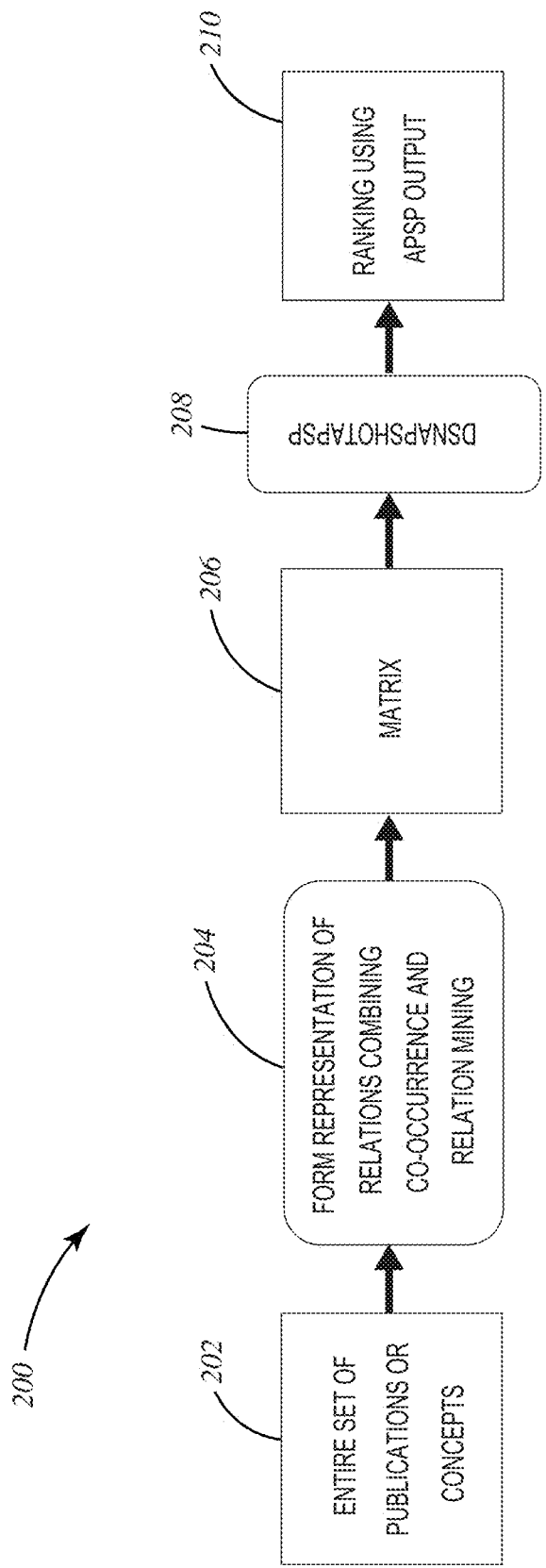
FIG. 2 shows a graphical representation of a method of knowledge mining with DSNAPSHOT all-pairs shortest path output.

Referring to FIG. 2, an exemplary high level graphical representation of a knowledge mining method 200 implementing the DSNAPSHOT algorithm in order to determine all-pairs shortest path of a knowledge graph is depicted. The method includes taking an entire set of publications or concepts 202 (e.g., in text format with English words) and forming a representation of relations 204 combining co-occurrence and relation mining, e.g., a knowledge graph representation or modelling of the repository or collection of text documents (typically in the millions or more) and relationships among them. That is, instead of starting the knowledge mining process with a particular concept or article, the process begins with an entire knowledge graph. The knowledge graph can include relationship information using concept co-occurrence, relation mining, and citation information or any combination thereof. The knowledge graph can be represented as a matrix 206. When the DSNAPSHOT algorithm 208 is executed on the matrix 206, a ranking using all-pairs shortest path can be generated and output 210, e.g., to a user interface presented to a user on a device in communication over a network with the computer executing the DSNAPSHOT algorithm.

In one configuration, a supercomputer executing the DSNAPSHOT algorithm can achieve 136 Petaflop/s in single-precision taking about 21.3 minutes to process a large graph composed of 4.43 million vertices, which involves execution of 170 exa-floating-point operations. It can be estimated that for an 18 million vertex knowledge graph, it will take about 18 hours to compute a DSNAPSHOT APSP. That is, leveraging graphics processing unit acceleration and communication enables optimizations for a two-dimensional distributed FW algorithm. This allows efficient scaling of an APSP algorithm to inputs with millions of vertices.

For example, by modeling the Semantic MEDLINE dataset as a matrix suitable for HPC algorithms, the extraction of useful information at scale can be enabled. Modeling of other datasets can similarly enable the extraction of other useful information at scale utilizing the DSNAPSHOT APSP algorithm.

It is well understood that there is an equivalence between finding shortest paths in a knowledge graph and solving a system of linear equations. While APSP is the semiring-equivalent of matrix inversion, no truly sub-cubic (Strassen-like) algorithm for APSP is known. The best-known complexity of APSP for the dense case is parallel case, the complexity is O(log n).

One aspect of the present disclosure is generally directed to an implementation of DSNAPSHOT using a message passing interface ("MPI") for expressing distributed memory parallelism. The MPI processes are logically arranged in a two-dimensional (2D) process grid. On this 2D process grid, DSNAPSHOT distributes the input matrix A in a block cyclic fashion.

Figure 5:
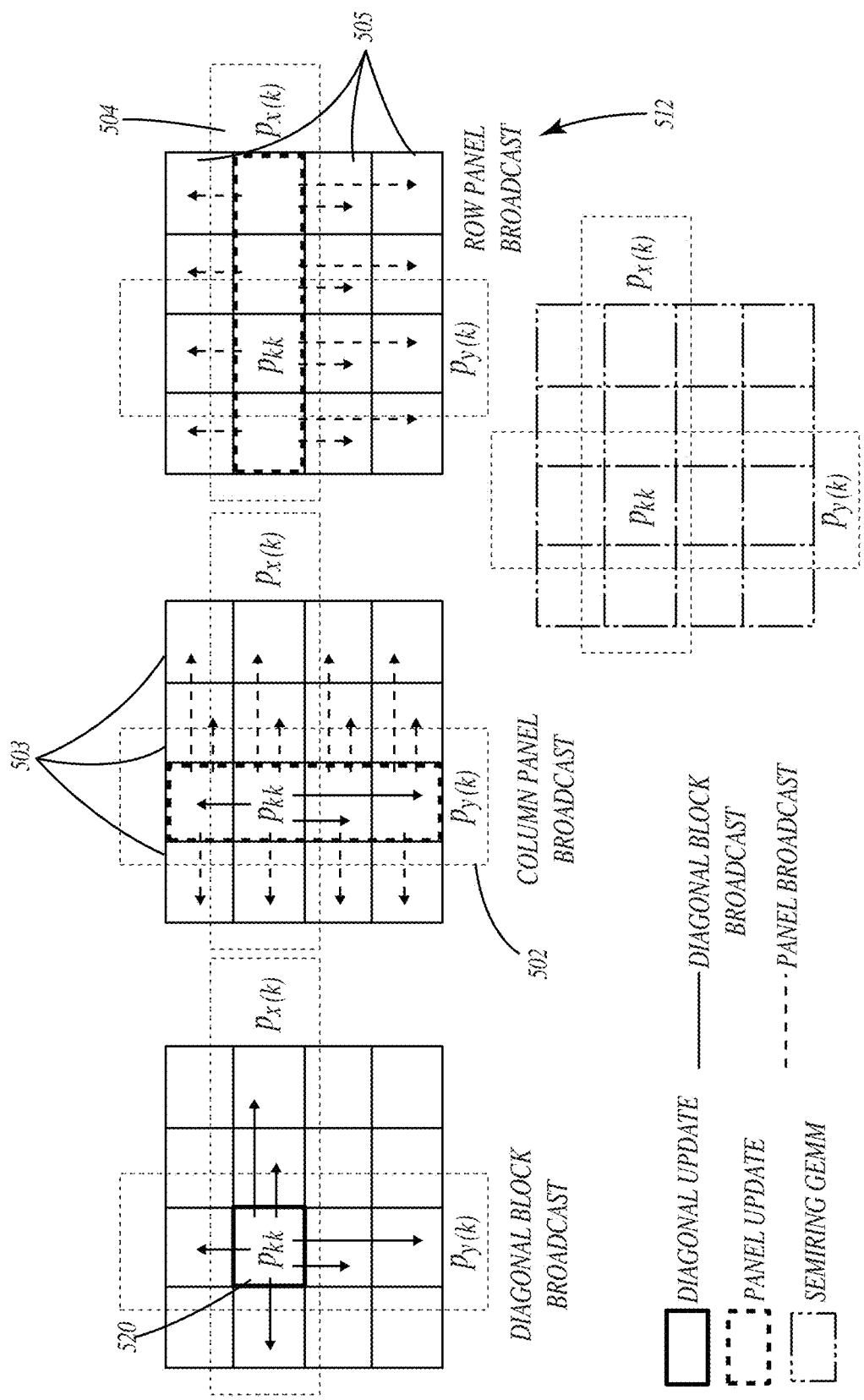
FIG. 5 shows a representative illustration of communication patterns in a DSNAPSHOT embodiment in accordance with the present disclosure.

Referring to FIG. 5 and the baseline 2D Distributed Block FW Algorithm set forth in Table III, various MPI communicator and communication patterns involved in one exemplary implementation of a DSNAPSHOT algorithm in accordance with the present disclosure are shown. The 4×4 grid of squares illustrated in FIG. 5 represent a grid of 16 different processes, with each square representing a distinct process in one block b of processes. The processes can be addressed by column and row. For example, a column of four processes 514 can be referenced by $P_y(k)$ while a row of four processes 506 can be referenced by $P_x(k)$. A diagonal group of processes 520 can be referenced by $p_{kk}$. The number of squares is a tunable parameter in DSNAPSHOT algorithms. In this instance, the 4×4 grid of squares represents a set of 16 processes of a larger process input matrix. That is, in this example, a block includes 16 processes, which the MPI assigns to different physical processors for processing.

The $k^{th}$ process row $P_x(k)$ is shown by dotted rectangles 506 and the $k^{th}$ process column $P_y(k)$ is shown by dotted rectangles 516. In the $k^{th}$ diagonal update step, process $p_{kk}$ 520 performs a local FW computation and broadcasts it across $P_y(k)$ and $P_x(k)$. That is, the processor performing the diagonal update communicates its results to the other processes shown by the arrows. In alternative embodiments, additional or fewer transmissions may be sent. Similarly, in the $k^{th}$ panel broadcast, each process in $P_x(k)$ broadcasts a calculated A(:, k) panel to their process column $P_y(k)$, and similarly each process in $P_x(k)$ broadcast the calculated A(k, :) panel to their process row $P_x(k)$. That is, each row panel process communicates to the three other processes that share a column and each column panel process communicates to the three other processes that share a row.

On obtaining the $k^{th}$ panels, A(k,:) and A(:, k), a process can update the blocks of A(k+1: $n_s$, k+1: $n_s$) that it owns. This update can be referred to as the MinPlus Outer Product. The MinPlus Outer Product can be obtained by executing semiring general matrix multiplication ("SRGEMM") on a graphics processing unit ("GPU").

Table III below sets forth a baseline FW algorithm upon which the DSNAPSHOT algorithm is based. The 2D distributed block FW algorithm includes pseudocode for assigning blocks of processes to different processors, the processes including diagonal update, panel update, and a MinPlus outerProduct. The steps in the algorithm are executed by considering the portion of the input graph and the coordinate of the process in the logical MPI process arrangement. The "if" conditions confirm the state and execute the appropriate sections of the parallel algorithm. For example, referring to FIG. 5 and Algorithm 2 below, the "if" condition in step 8 corresponds to the column panel broadcast and the "if" condition in step 14 corresponds to the row panel broadcast. In response to the "if" condition being true, i.e. a process being assigned to the active $k^{th}$ column 502 (step 8)_or the active $k^{th}$ row 504 (step 14), then the algorithm distributes, e.g., broadcasts, its results. Specifically, for the column panel broadcast 510, the results of the active $k^{th}$ column processes 502 are broadcast to the other columns 503 (steps 9-11), and for the row panel broadcast 512, the results of the active $k^{th}$ row 504 are broadcast to the other rows 505 (steps 15-17), which are illustrated by the column panel broadcast graphic 514 and the row panel broadcast graphic 506.

TABLE III

Algorithm 2 A Baseline 2D Distributed Block FW

| | |
|---|---|
| 1: | Input: Distributed sparse matrix A; |
| 2: | On each MPI Process $p_{id}$ do in parallel: |
| 3: | for k = 1, 2, 3 . . . $n_b$ do |
| 4: | Synchronize all processes |
| | Diagonal Update |
| 5: | if $p_{id}$ owns A(k,k) then |
| 6: | A(k,k) ← FW(A(k,k)) |
| 7: | Send A(k,k) to $P_x$(k) and $P_y$(k) |
| | Panel Update |
| 8: | if $p_{id} \in P_y$(k) then |
| 9: | Wait for A(k,k) |
| 10: | A(k,:) ← A(k,:) ⊕ A(k,k) ⊗A(k,:) |
| 11: | Send A(k,:) blocks to needed processes in $P_x$(:) |
| 12: | else |
| 13: | Receive A(k,:) blocks if needed |
| 14: | if $p_{id} \in P_x$(k) then |
| 15: | Wait for A(k,k) |
| 16: | A(:,k) ← A(:,k) ⊕ A(:,k)⊗A(k,k) |
| 17: | Send A(:,k) blocks to required processes in $P_y$(:) |
| 18: | else |
| 19: | Receive A(:,k) blocks if required |
| | MinPlus Outer Product |
| 20: | for i ={1, 2 . . . , $n_b$}, i ≠ k do: |
| 21: | for j ={1, 2 . . . , $n_b$}, j ≠ k do: |
| 22: | A(i,j) ← A(i,j) ⊕ A(i,k) ⊗ A(k,j) |

A biomedical knowledge graph was constructed using the Semantic MEDLINE2 database. One version of Semantic MEDLINE contains nearly 98 million predications (concept-to-concept relations) extracted using the SemRep library from over 18 million biomedical abstracts. The dataset was enriched with concepts and relations extracted using SemRep from the CORD-19 dataset of publications on COVID-19, SARS-COV-2, and other coronaviruses. Specifically, one version from Jun. 30, 2020, contains over 130 thousand publication abstracts.

The knowledge graph construction from the two datasets will now be described. The exemplary knowledge graph is composed of two types of nodes: (1) concept nodes, which represent unique biomedical terms, for example, drugs, genes, diseases, and symptoms (there are 127 different concept types in this embodiment). There are over 290 thousand unique concept nodes; and (2) abstract nodes, which represent the 18 million PubMed abstracts.

Figure 6:
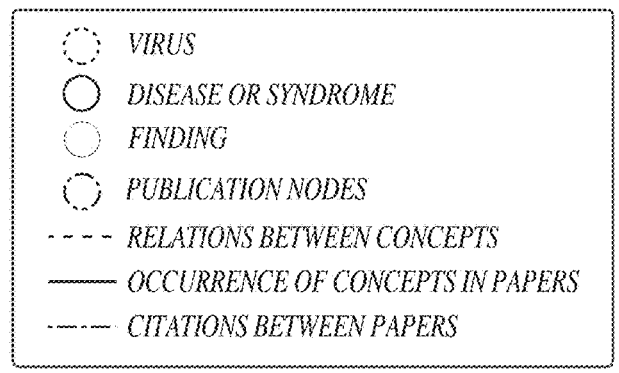
FIG. 6 shows an exemplary knowledge graph for use in connection with embodiments of the present disclosure.
Figure 6:
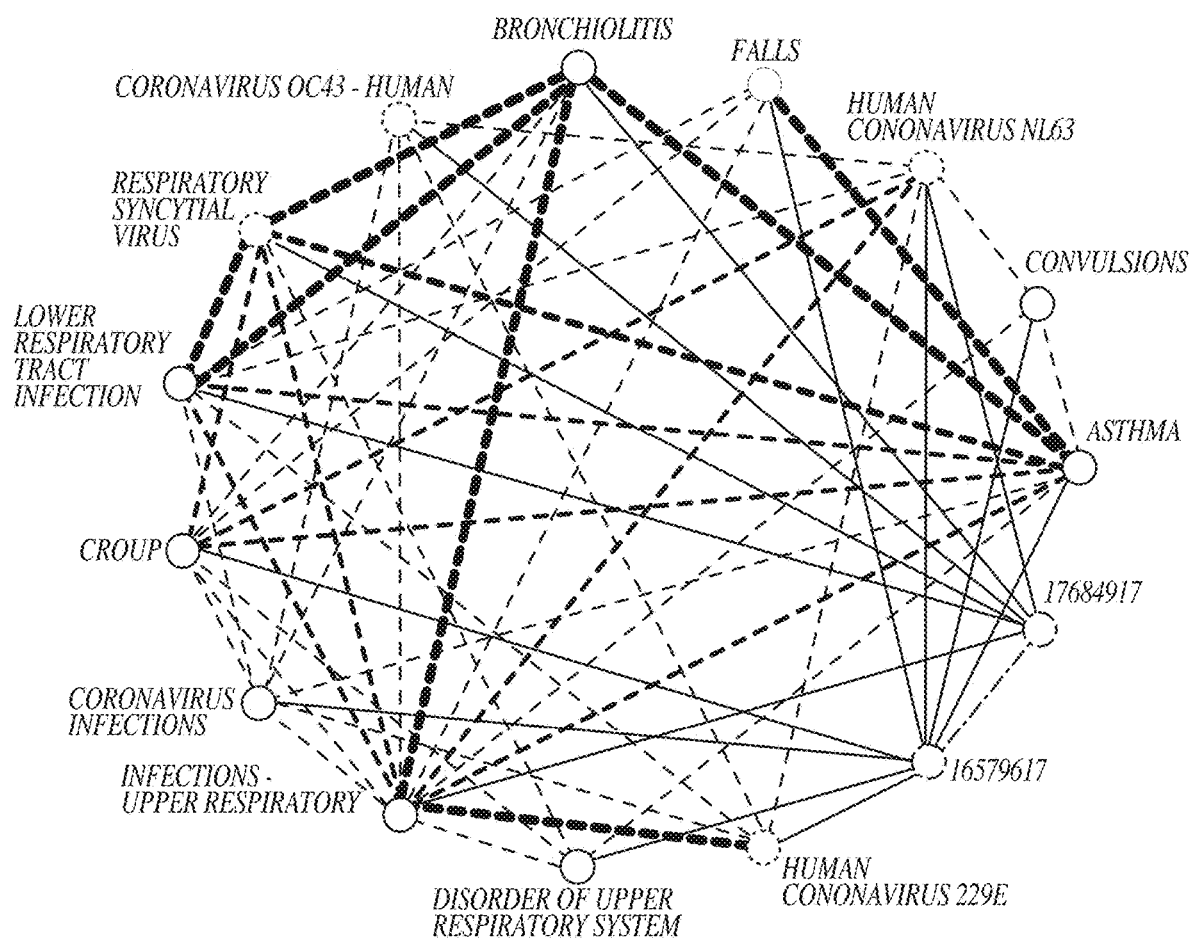

A small portion of the exemplary knowledge graph is depicted in FIG. 6. The nodes in this exemplary knowledge graph can be connected in three different ways: (1) concept to concept relations, (2) concept to abstract relations, and (3) abstract to abstract relations. Each are discussed in more detail below in turn.

The connections between concepts represent relationships described in abstracts, for example, the sentence, "Zika virus is a member of the family Flaviviridae," would result in a "part of" relation between "Zika" and "Flavivirida," while both concepts would be tagged with "virus" label. In the Semantic MEDLINE database, these relations are represented as predications. There are 14 million unique concept to concept relations in this exemplary graph which were extracted from the 98 million Semantic MEDLINE predications. For the shortest path computation, the system assigns these edges Jaccard similarity score of the connected concepts, which is calculated as the number of times the two concepts appear together in a predication divided by the total number of predications these concepts appear in. For illustration purposes, these connections are represented in solid connection lines.

The connections between abstracts and concepts represent occurrence of concepts in abstracts. For example, if the above sentence, "Zika virus is a member of the family Flaviviridae," appeared in abstract with PubMed ID 111, there would be a connection between the abstract node "PMID111" and concepts "Zika" and "Flaviviridae." There are 196 million unique concept to paper connections in the graph. For the shortest path computation, edges are assigned a weight representing the number of times a concept appears in the abstract divided by the total number of concepts appearing in the abstract. For illustration purposes, these connections are represented in dashed connection lines with the weight represented by the weight/thickness of the line.

The connections between abstracts represent citation relationships between abstracts. For example, if an abstract with PubMed ID 111 cited an abstract with PubMed ID 222, there would be a connection between those two abstracts in the graph. There are 3 million citation relations in the exemplary graph. For the shortest path computation in this embodiment, citations are treated as undirected edges and assigned a weight calculated as $1/(N_{P1}+N_{P2})$, where N represents the total number of citation relations of abstract p. These relations are represented in dash-dot connection lines.

In total, the graph is composed of nearly 18.5 million nodes (over 290 thousand unique concepts and over 18 million publications), and 213 million edges. FIG. 6, which represents a small portion extracted from the complete knowledge graph, shows the types of nodes and all three types of relations.

Distributed Accelerated Semiring all-Pairs Shortest Path (DSNAPSHOT)

The Distributed Accelerated Semiring All-Pairs Shortest Path (DSNAPSHOT) algorithm is a 2-D distributed-memory FW variant of Algorithm 2 set forth in Table III that offloads semiring GEMM computations to graphics processing unit(s). The system performs computations on a graphics processing unit ("GPU") or central processing unit ("CPU") based on their nature and offloading costs. The SemiRing general matrix multiplication (SRGEMM) of has generally the same acceleration opportunities of classical GEMM due to its high arithmetic intensity and data access pattern. However, the diagonal update can be performed on smaller portions of the matrix and involves sequential computations that are difficult to accelerate on a GPU. Hence, all panel updates and the MIN-PLUS outer product can be performed on a GPU using SRGEMM, as discussed herein.

DSNAPSHOT can be flexibly implemented so that it can perform communication among CPUs and GPUs. In Table IV one embodiment of the DSNAPSHOT algorithm is set forth and labeled Algorithm 3. Even though panel updates are configured to be performed on a GPU in the current DSNAPSHOT embodiment, to broadcast the results on the process rows $P_x$(k) or $P_y$(k), there is a memory transfer to CPU involved because of an engineering limitation. This variant of the algorithm is referred to as DSNAPSHOT.

Referring to FIG. 5 and algorithm 3 set forth in of Table IV, essentially any step in the DSNAPSHOT algorithm can be executed by considering the portion of the input graph and the coordinate of the process in the logical MPI process arrangement.

TABLE IV

Algorithm 3 Distributed Accelerated Semiring
All-Pairs Shortest Path (DSNAPSHOT)

| | |
|---|---|
| 1: | Input: Distributed sparse matrix A; |
| 2: | On each MPI process $p_{id}$ do in parallel: |
| 3: | for k=1, 2, 3 . . . $n_b$ do |
| 4: | Synchronize all processes |
| | Diagonal Update |
| 5: | if $p_{id}$ owns A(k,k) then |
| 6: | Copy Diagonal Blocks from GPU $A_{GPU}$ (k,k) to CPU A(k,k) |
| 7: | A(k,k) ← FW(A(k,k)) |
| 8: | Send A(k,k) to $P_x$(k) and $P_y$(k) |
| | Panel Update |
| 9: | if $p_{id} \in P_y$(k) then |
| 10: | Wait for A(k,k) |
| 11: | Copy A(k,k) from CPU to GPU $A_{GPU}$ (k,k) |
| 12: | SRGEMM_GPU($A_{GPU}$(k,k), $A_{GPU}$ (k,:), $A_{GPU}$ (k,:)) |
| ▷ | // $A_{GPU}$ (k,:) ← $A_{GPU}$ (k,:) ⊕ $A_{GPU}$ (k,k) ⊗ $A_{GPU}$ (k,:) |
| 13: | Copy $A_{GPU}$ (k,:) from GPU to CPU A(k,:) |
| 14: | Send A(k,:) blocks to needed processes in $P_x$(:) |
| 15: | else |
| 16: | Receive A(k,:) blocks if needed |
| 17: | if $p_{id} \in P_x$(k) then |
| 18: | Wait for A(k,k) |
| 19: | Copy A(k,k) from CPU to GPU $A_{GPU}$ (k,k) |
| 20: | SRGEMM_GPU($A_{GPU}$ (:,k), $A_{GPU}$ (k,k), $A_{GPU}$ (:,k)) |
| ▷ | // $A_{GPU}$ (:,k) ← $A_{GPU}$ (:,k) ⊕ $A_{GPU}$ (:,k) ⊗ $A_{GPU}$ (k,k) |
| 21: | Copy $A_{GPU}$ (:,k) from GPU to CPU A(:,k) |
| 22: | Send A(:,k) blocks to required processes in $P_y$(:) |
| 23: | else |
| 24: | Receive A(:,k) blocks if required |
| | MinPlus Outer Product |
| 25: | for i={1, 2 . . . , $n_b$}, i ≠ k do: |
| 26: | for j={1, 2 . . . , $n_b$}, j ≠ k do: |
| 27: | SRGEMM_GPU ($A_{GPU}$ (i,k), $A_{GPU}$ (k,j), $A_{GPU}$ (i,j)) |
| ▷ | // A(i,j) ← A(i,j) ⊕ A(i,k) ⊗ A(k,j) |

The pseudocode of the embodiment of the DSNAPSHOT algorithm set forth in Table IV will now be described in detail. The algorithm can be described generally in four distinct sections: (1) MPI initialization and data distribution (lines 1-4); (2) diagonal update (lines 5-8); (3) panel update (lines 9-24); and (4) MinPlus Outer Product (lines 25-27).

The message processing interface ("MPI") initialization and data distribution section accepts a distributed sparse matrix A. That is, a matrix that includes mostly zero coefficients and that is stored distributively in one or more resilient distributed datasets. Each computer is assigned one or more MPI process(es) with different process identifiers ("pid") for parallel processing. This parallel processing is repeated iteratively over a number of iterations nb based on the number of blocks b. In the current embodiment, each MPI processes will always be performing one of the Diagonal Update, Panel Update, or MinPlus Outer Product. The panels A(k,k), A(k, :), A(:, k) represent diagonal, column, and row panels respectively. Essentially, every MPI process will belong to a row and column panel.

The pseudocode for the Diagonal Update uses the term "owns" to refer to a portion of the input matrix that a particular MPI process is in charge, i.e., owns. MPI will coordinate and arrange to have a physical processor execute the Diagonal Update, Panel Updates, and the MinPlus Outer Product process and ensure that the process that owns non-diagonal blocks will not execute the diagonal update.

Since DSNAPSHOT is a parallel algorithm, any MPI process can be in one of the two states—computation or communication. Within computation it can perform one of the diagonal update, panel update or min-plus outer-product. Communication is performed asynchronously. When the appropriate data is ready after the computation, the communication portion will transmit the data. Similarly, when the communication portion receives data, it triggers the corresponding computation. The algorithm defines a protocol that automatically enforces the ordering of the processes. That is, every process knows to whom it has to send data/results and every process is also aware from whom it will be receiving data/results.

The communication and the computations can be done by different hardware components. Accordingly, computation and communication can be performed concurrently. Since computation and communication are performed concurrently, every computation can be performed with already received data while the communicator is waiting to receive or send the next batch of data.

GPU Acceleration. The primary compute kernel in the blocked Floyd-Warshall algorithm set forth in Table IV labeled DSNAPSHOT is matrix multiplication over the tropical semiring. Blocked refers to every MPI process further dividing the portion of its input matrix into blocks. Although this (min, +) SRGEMM kernel is semantically different from the traditional level-3 BLAS multiply-accumulate GEMM operation, it lends itself to the same acceleration opportunities due to its high arithmetic intensity and identical data access pattern. The system of the present disclosure implements MIN-PLUS SRGEMM by extending an NVIDIA Cutlass open-source linear algebra framework. In other embodiments, other linear algebra frameworks can be leveraged.

To implement DSNAPSHOT, modifications were made to traditional basic linear algebra subprograms ("BLAS") GEMM of the form $C=\alpha AB+\beta C$ with semiring GEMM. In particular, the following modifications to Cutlass (a public library) were made to facilitate implementation of an SRGEMM kernel capable of executing the DSNAPSHOT algorithm. Some of the modifications are embedded in the algorithm on the SemiRing GEMM step after the panel update.

Semiring Operators in Matrix Multiplication: Support for overriding the ring operators in matrix multiply for other semiring operators in a composable fashion.

Identity Values: Support for custom initialization and padding values as identity values of ring operations. This involves initializing registers with instead of the default zero.

Epilogue Operator: Addition of semiring BLAS epilogue operator in the tropical semiring (min, +) for an elementwise min with the C matrix.

Communication Optimizations. The embodiment of DSNAPSHOT set forth in Algorithm 3 can perform a high volume of communication at a level of complexity in the $O(n^2/P_x + n^2/P_y)$ range. The communication complexity will be discussed in more detail below. Suffice it to say, during scaling to large nodes, The DSNAPSHOT algorithm spends more time in communication over computation. At least the following alleviation techniques can address this: (a) Lookahead-accelerating the critical path of diagonal update and broadcast; (b) a ring broadcast protocol; (c) Rank Mapping; and (d) optimizing intra-node communication. Each of these alleviation techniques are discussed in turn below.

Lookahead Technique: A lookahead technique can accelerate execution of the critical path in the computation and overlap communication with computation. The diagonal and the panel update lies in this critical path. When the matrix A(k, :) in iteration k has been updated by the column processes $P_y$ and broadcast to row processes $P_x$ as depicted in the column panel broadcast of FIG. 5, the globally next urgent job is to perform both the diagonal and panel update and communication of the of panels A(k+1, k+1), A(k+1,:)

by the next column process P. A similar approach is also applicable for row process $P_x$ for block A(:, k+1).

In the case of lookahead DSNAPSHOT, as soon as process $P_{k+1,k+1}$ receives the panel A(k,:) and panel A(:, k), the subsequent process $P_{k+1,k+1}$ can perform a SRGEMM using these panels to obtain the look ahead panel A(k+1, k+1). The diagonal update on panel A(k+1, k+1) is performed and broadcast to row and column processes in $P_{x+1}$ and $P_{y+1}$ respectively.

Then for, $P_{x+1}$ and $P_{y+1}$, the panels A(k,:) and A(:, k) and the updated diagonal block A(k+1, k+1) can be utilized to perform the panel updates/broadcast of panels A(k+1,:), A(:, k+1) using SRGEMM before the MIN-PLUS Outer Product on its $k^{th}$ iteration. In this way, the diagonal and panel broadcasts can be conducted efficiently and the global critical path can be accelerated.

Accordingly, the lookahead DSNAPSHOT, involves invocation of some small block SRGEMM and additional buffer management. In exchange, the lookahead can accelerate execution of the critical path in the computation and overlap communication with computation.

Ring Broadcast over Tree Based Broadcast: Traditional libraries for message passing, such as the MPI BCast library are less efficient for DSNAPSHOT because it utilizes a kd-tree pattern (also referred to as a hyper-cube algorithm) that costs log P $(\alpha+w\beta)$ for broadcasting w units of data among P processes. Such an algorithm balances latency ($\alpha$ term) and bandwidth ($\beta$ term) costs. In contrast, bandwidth is of greater concern for DSNAPSHOT, thus a broadcast based on ring-pattern that costs $(P-1)\alpha+w\beta$, provides superior bandwidth costs. The higher latency cost in the ring broadcast can be mitigated by pipelining broadcasts from different iterations. The current embodiment of DSNAPSHOT implements a non-blocking version of the ring-broadcast.

Rank Placement: When creating a two-dimensional logical process grid using a message passing interface ("MPI"), by default the MPI ranks within a node will be placed in a process row or process column. However, this rank placement does not consider the data transfer via the network interface card (NIC) in a single node. To reduce data transfer via NIC, ranks within a node are arranged in a 2D grid with the same aspect ratio as the logical process grid. Put another way, if $Q_r \times Q_c$ ranks per physical node with a total of $P_x \times P_y$ logical MPI processes, then NIC data transfer is substantially reduced or minimized when $Q_r \approx Q_c$. In a high end supercomputer, this can be achieved using a so-called explicit resource file ("ERF"). Purposeful rank placement benefits a majority of the various DSNAPSHOT variations.

Optimizing Intra-Node Communication: To reduce data transfer via NIC, the system architecture implementing the DSNAPSHOT algorithm efficiently exploits architectural features for intra-node communication. Specifically, for intra-node GPU to GPU data and control code transfers in processor systems, NVlink can be used, and within node CPU to CPU transfer, hyper transport can be used. In alternative embodiments, GPUDirect or another protocol can be utilized for efficient intra-node communication.

DSNAPSHOT Analysis. The computation cost, communication cost, and total cost analysis of an embodiment of DSNAPSHOT can be determined according to the following formulas. Before assessing those characteristics of DSNAPSHOT, it is helpful to assess the computation cost, communication cost, and total cost of the FW algorithm for context, i.e., algorithm 2, the baseline 2D distributed block FW algorithm presented in Table III above.

The computation cost for the blocked FW algorithm can be computed by assessing the number of floating-point operations ($2n^3$) distributed among P processes. Accordingly, because the computation is uniform and load-balanced, the computation cost for the blocked FW algorithm can be represented as follows:

$$T_{comp} \frac{2n^3}{P} \gamma \qquad (2)$$

where $\gamma$ is the cost of unit floating-point operations.

The communication cost for the blocked FW algorithm can be computed by assessing the block-size b used for block-cyclic data distribution, then utilizing algorithm 2 to perform the $$\frac{n}{b}$$

outer loop iterations. In each of the iterations, each process participates in two broadcasts $$\frac{nb}{P_x}$$

across process row and $$\frac{nb}{P_y}$$

across process column. In the ring broadcast, the total cost of the two broadcasts is $$2\alpha + \beta\left(\frac{nb}{P_x} + \frac{nb}{P_y}\right),$$

where alpha $\alpha$ is the setup cost of sending a message and beta $\beta$ is the cost of sending a unit float word. Since the outer iteration runs for $$\frac{n}{b}$$

iterations, the total communication cost can be represented as:

$$T_{comm} = 2\frac{n}{b}\alpha + \beta n^2 \left(\frac{1}{P_x} + \frac{1}{P_y}\right) \qquad (3)$$

The total cost depends on the number of iterations n and number of processes P. Essentially, either the computation cost $T_{comp}$ or communication cost $T_{comm}$ will dominate the total cost. In an ideal case, the system can be configured to overlap the computation with the communication, or vice-versa. In the case where they can be substantially or entirely overlapped, the total cost can be represented by the following equation:

$$T_{ideal} = \max\left\{\frac{2n^3}{P}\gamma, 2\frac{n}{b}\alpha + \beta\left(\frac{n^2}{P_x} + \frac{n^2}{p_y}\right)\right\} \quad (4)$$

Where communication and computation cannot be significantly overlapped, the total cost can be represented by the following equation:

$$T_{worst} = T_{comp} + T_{comm} = \frac{2n^3}{P}\gamma + 2\frac{n}{b}\alpha + \beta\left(\frac{n^2}{P_x} + \frac{n^2}{P_y}\right) \quad (5)$$

Figure 3:
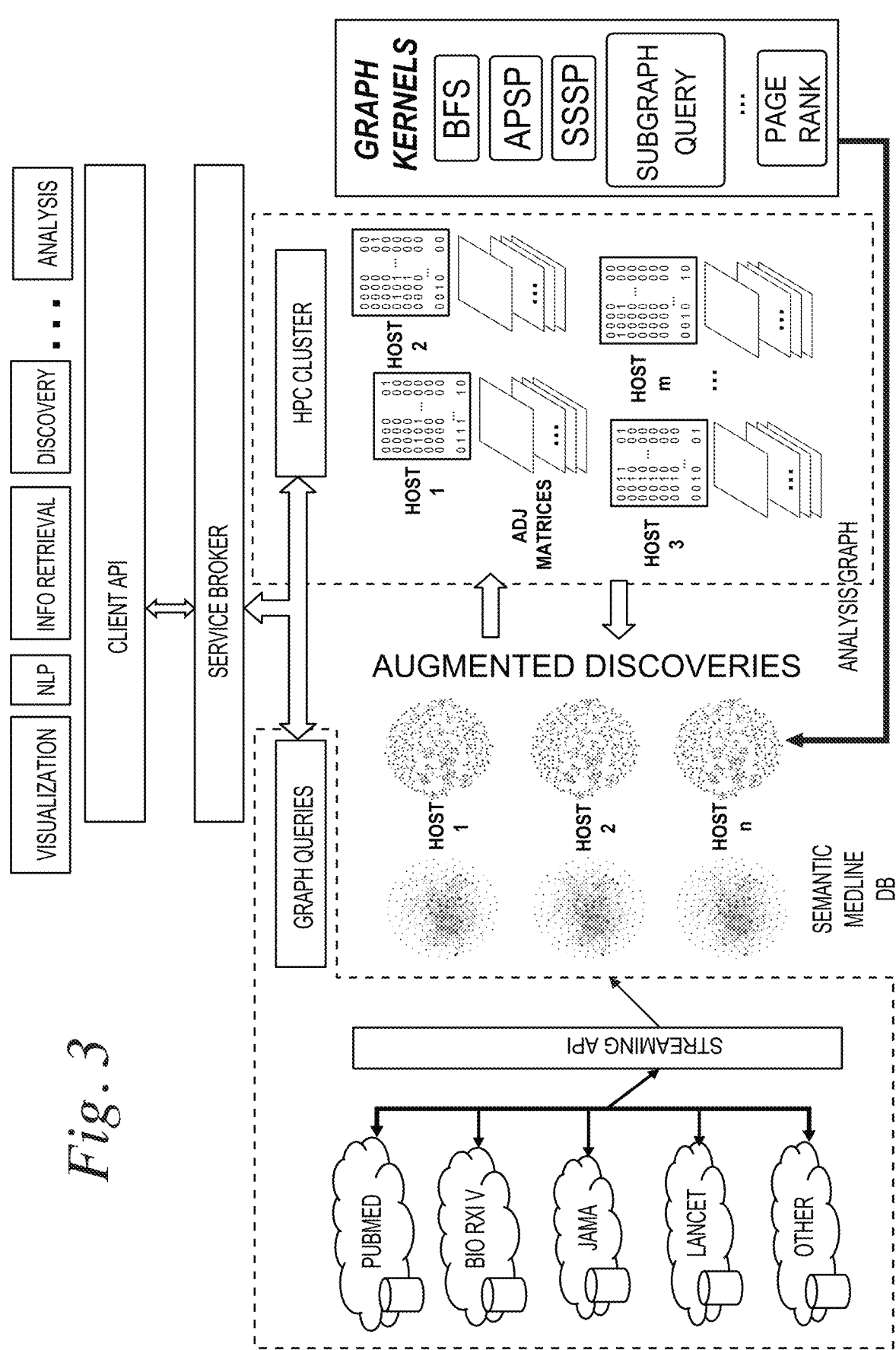
FIG. 3 shows an exemplary workflow of one embodiment of a system for executing the DSNAPSHOT algorithm.

An exemplary system architecture and workflow for one embodiment of DSNAPSHOT is illustrated in FIG. 3. The workflow incorporates (a) streaming publication data from different sources and the knowledgegraph representation of these biomedical texts; (b) various client services like natural language processing and visualization; and (c) a backend query engine for operating on the knowledge graph, which invokes operations such as the DSNAPSHOT algorithm. The depicted workflow is configured for processing biomedical knowledge graph analytics. But without loss of generality, DSNAPSHOT and its various alternative embodiments can be extended to any domain and cross-domain literature analysis beyond the biomedical domain.

The workflow includes a client that includes a user interface with visualization, NLP, information retrieval, discovery, and analysis modules. A client application programming interface can communicate with a service broker to handle knowledge graph queries and communication with a high performance computing cluster, such as Summit. A streaming API can accept publications from various databases, such as Pubmed, BioRxiv, JAMA, LANCET, and essentially any other source relevant to the particular knowledge graph being supplemented. These sources can be integrated into a semantic database, such as the semantic MEDLINE database, which can be represented as a knowledge graph that is hosted in a distributed manner.

The knowledge graph kernels can include a Breadth First Search (BFS), APSP, Single Source Shortest Path (SSSP), Subgraph query, and PageRank modules, among other modules. BFS helps in determining a path between two vertices like the number of people someone needs to make friendship to establish connection with an unknown stranger like in social networks. Similarly, page rank is an indication of how influential a vertex in a graph is. These modules can handle the knowledge graph analysis by leveraging the HPC cluster as discussed herein.

Figure 4:
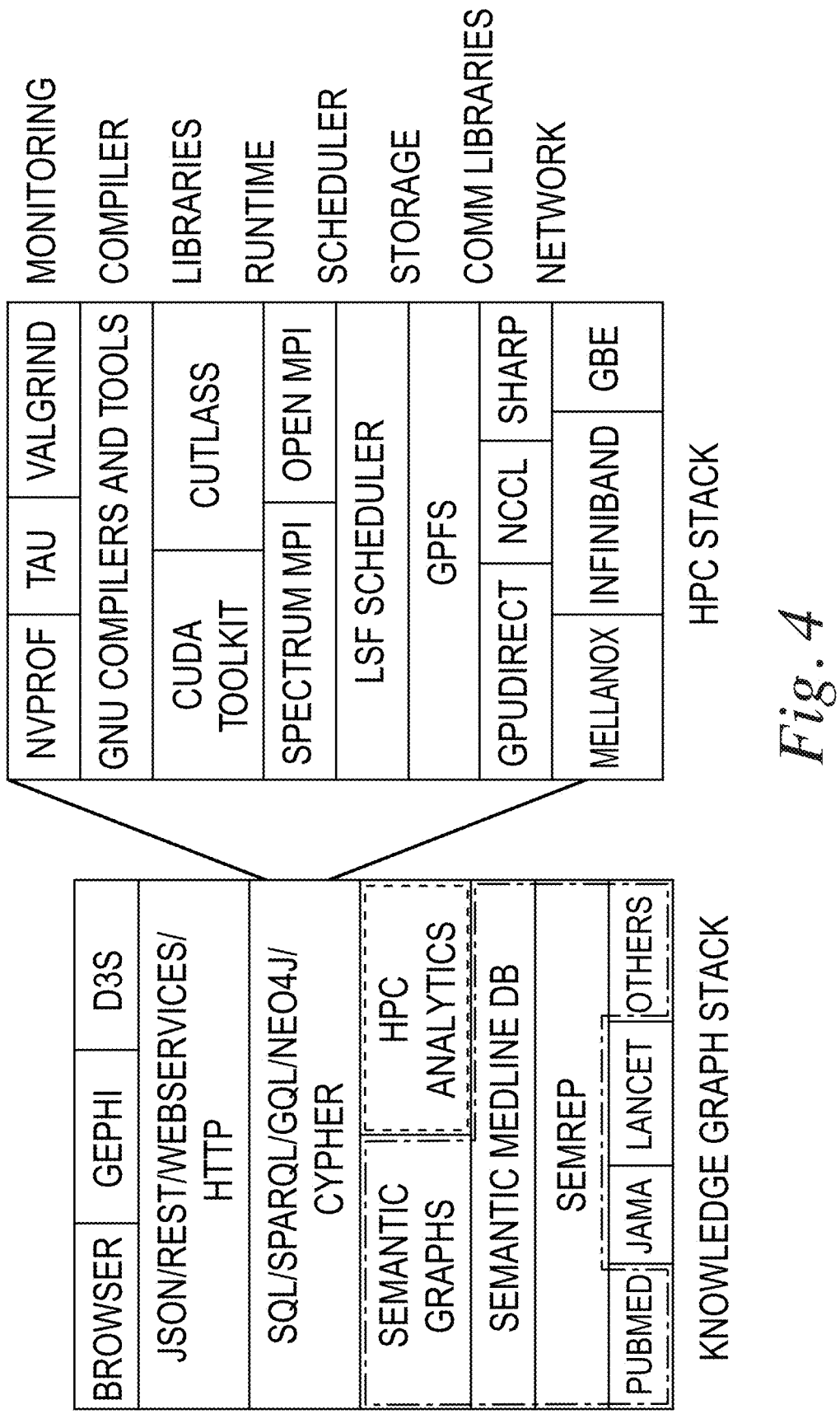
FIG. 4 shows a representative diagram showing the integration of an exemplary knowledge graph stack and a high performance computing environment stack.

FIG. 4 illustrates a representative block diagram of a DSNAPSHOT software stack. In the current embodiment, the computing environment software versions used are GCC 6.4.0, IBM Spectrum MPI 10.2.0.0, and CUDA 10.1.243. Summit's jsrun tool can be used for application launch. The HPC analysis stack includes monitoring components, a compiler(s), various software libraries, runtime interfaces (e.g., Spectrum MPI and Open MSI), a scheduler, storage, communication libraries, and network components/protocols.

DSNAPSHOT's performance can be assessed in the context of growth trends in scientific articles, which are generally accepted to grow at a generally exponential rate over time. To provide context, in general, the amount of scientific literature doubles about every nine years, and there have been estimates that the number of English scientific articles in existence is greater than 114 million articles. The present disclosure sets forth a framework for providing scalable knowledge graph analytics, even with these types of growth rates. DSNAPSHOT has favorable single-node efficiency compared to other APSP baselines.

Additional Information about a variety of different DSNAPSHOT embodiments is presented herein. The lookahead DSNAPSHOT ("LA") variation is an extension of DSNAPSHOT with the lookahead feature implemented as discussed above. Another DSNAPSHOT variation, referred to as LA+Ring, utilizes the lookahead feature and also leverages a ring broadcast feature in connection with the message passing interface ("MPI") broadcast. In all three algorithms, DSNAPSHOT, LA, and LA+Ring, all MPI communications can be performed using host side buffers. Any GPU device buffers for communication can be staged through host memory via a device to host memory copy.

Two additional embodiments of DSNAPSHOT leverage CUDA-aware MPI communication, performing communication directly from GPU device buffers. In both the cases, these embodiments take advantage of GPUDirect communication. Specifically, the GPU buffer is directly passed as input for the MPI broadcast to the CUDA-aware IBM spectrum MPI implementation. A typical CUDA-aware MPI does not take a separate GPU stream as input. Therefore, to maintain parallelism the SRGEMM kernel is invoked in a dedicated stream. The CUDA-aware MPI broadcast DSNAPSHOT algorithm and the CUDA-aware MPI ring broadcast DSNAPSHOT algorithm embodiments can be referred to as GPUDirect and GPUDirect+Ring, respectively.

In the current embodiments, for both the weak and strong scaling up to 256 nodes, every node can have 12 MPI ranks and one GPU for every two ranks. Each MPI rank can be allocated six cores and the ratio of $p_r:p_c$ can be maintained as 4:3 per node. In other embodiments, these values can vary.

In some exemplary implementations with strong scaling, a knowledge graph of 300,000 vertices can be analyzed by any of the DSNAPSHOT embodiments. Overall, LA+Ring provides strong scaling even though LA may be slightly faster for smaller numbers of processors. In some implementations, a DSNAPSHOT algorithm can achieve 136 PF/s on 4,096 nodes on a system having about 24,500 GPUs. This amounts to roughly 90% of the parallel efficiency (i.e., out of 151 PF/s). Considering parallel efficiency relative to the smallest 16-node run, which achieves 6.12 TF/s per GPU, DSNAPSHOT attains about 92% parallel efficiency at 256 nodes.

Comparing the DSNAPSHOT variations against the cost models, the best and worst flop rates can be computed as $$\Gamma_{ideal} = \frac{2n^3}{T_{ideal}}$$

and $$\Gamma_{ideal} = \frac{2n^3}{T_{worst}},$$

based on the execution times T defined in equations (4) and (5) above. Table V presents exemplary flop rates for weak scaling DSNAPSHOT embodiments, which helps to demonstrates the degree to which computation and communication overlap. Accordingly, this model can be utilized to estimate the running time on an entire knowledge graph, such as the 18.5 million vertex biomedical knowledge graph referenced throughout this disclosure.

TABLE V

| N | P | $P_x$ | $P_y$ | n | Γ | $Γ_{worst}$ | $Γ_{ideal}$ |
|---|---|---|---|---|---|---|---|
| 16 | 192 | 12 | 16 | 300,000 | 0.55 | 0.4 | 0.7 |
| 32 | 384 | 16 | 24 | 378,624 | 1.05 | 0.8 | 1.3 |
| 64 | 768 | 24 | 32 | 476,928 | 2.06 | 1.6 | 2.7 |
| 128 | 1536 | 32 | 48 | 600,576 | 4.07 | 3.0 | 5.4 |
| 256 | 3072 | 48 | 64 | 756,480 | 7.69 | 5.7 | 10.8 |

Two additional exemplary implementations of DSNAPSHOT are discussed herein. In these exemplary embodiments, the DSNAPSHOT algorithm provides analytics on the CORD-19 dataset available online.

In one implementation, DSNAPSHOT is used to process a biomedical knowledge graph extracted from research articles published between 2010 to 2015. This graph is composed of 5,953,712 vertices and 445,236,526 edges.

In another implementation, DSNAPSHOT is used to analyze the shortest paths obtained for a knowledge graph built from the CORD-19 dataset. After removing duplicates, identified using their DOI indices, there were 155,771 articles in the dataset. The dataset was processed using SemRep and a knowledge graph generated. The data set was split into two subsets: research articles published up until 2005 (12,863 articles) and all articles published until 2020. Characteristics of the knowledge graphs are shown in Table VI:

TABLE VI

SIZE OF GRAPHS BASED ON CORD-19 DATA.

| Graph version | 2005 | 2020 |
|---|---|---|
| Concept vertices | 16,427 | 56,029 |
| Paper vertices | 12,863 | 155,771 |
| Concept-concept edges | 25,297 | 172,254 |
| Concept-paper edges | 140,095 | 1,535,064 |
| Paper-paper edges | 1,638 | 18,666 |

By comparing the DSNAPSHOT results on the two datasets, information about how many direct new connections between pairs of concepts have formed since 2005 can be extracted. That is, by measuring the characteristics of the shortest paths between pairs of concepts in the 2005 version of the graph and comparing the shortest paths between pairs of concepts in the current version of the graph, information about direct connections formed in the future, relative to 2005 can be uncovered.

Between 2005 and 2020, there were 42,077 new direct edges between the 16,427 concepts that existed in 2005. To illustrate that shorter paths are indicative of future connections, the following two sets of shortest paths from the 2005 graph can be extracted:

Shortest paths between pairs of concepts that do not have an edge between them in the 2005 version of the graph but do have a direct edge in the 2020 version of the graph (there are 42,077 such paths); and Shortest paths between random pairs of concepts that do not have a direct connection between them in either version of the graph (42,077 such paths selected to match the size of the first set).

Figure 7:
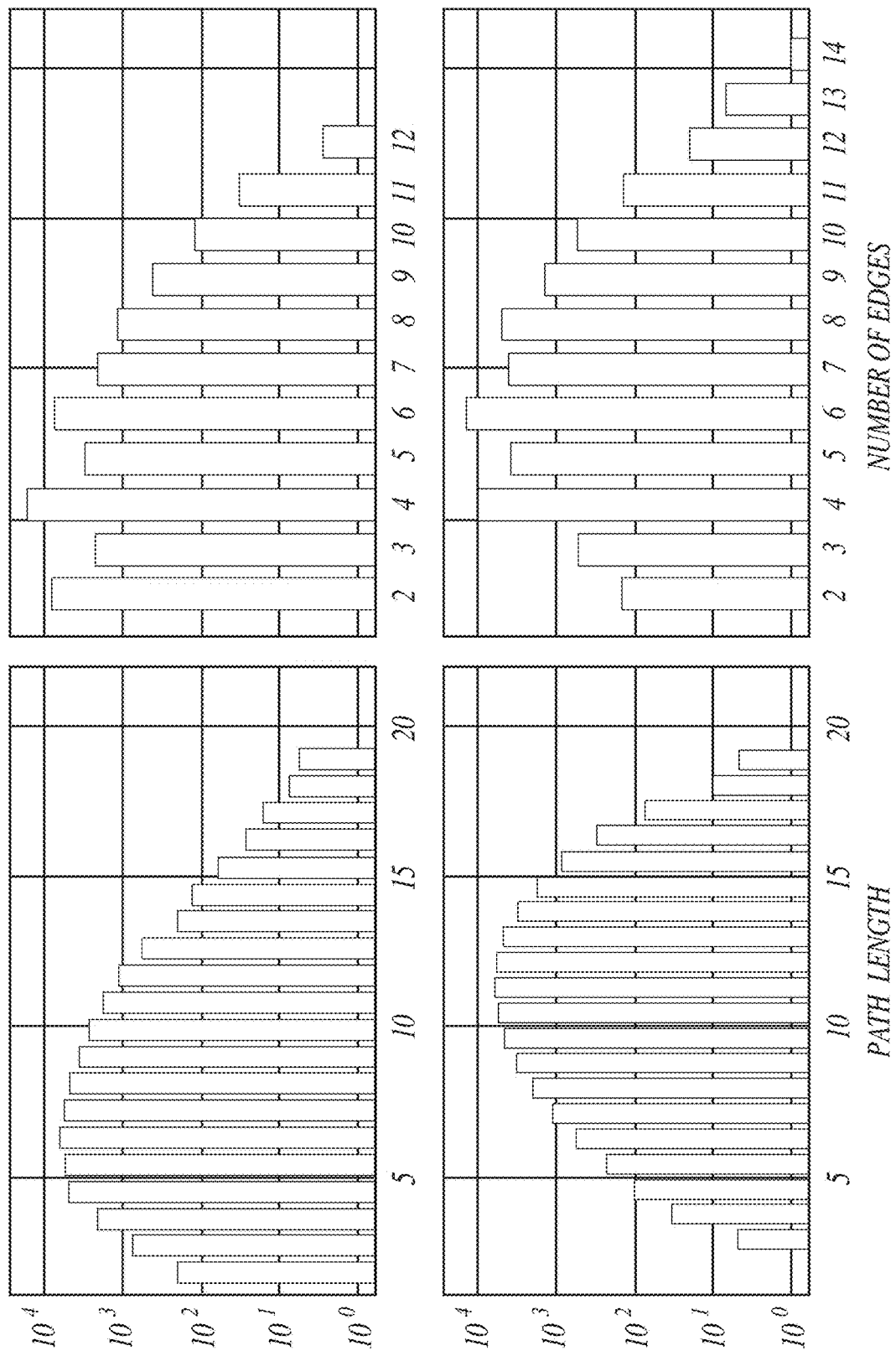
FIG. 7 shows graphs comparing path length and number of edges for a knowledge graph at two points in time.

FIG. 7 shows the distribution of path length (x-axis, left-side plots) and number of edges (x-axis, right-side plots) in both sets against the number of concept pairs in the two sets (y-axis, all plots). It can be seen the first set is slightly skewed towards shorter paths, while the second set is skewed in the opposite direction. Furthermore, very short paths do not appear in the second set. The difference in the distributions can be confirmed by applying the Kolmogorov-Smirnov test. Accordingly, the shortest path information available from DSNAPSHOT analysis can aid in uncovering novel relations between concepts, enabling the discovery of meaningful relations across a corpus, such as a biomedical corpus. DSNAPSHOT is highly performant and scalable, achieving at least 136 PF/s, setting a new high-watermark for FW-based APSP at the full-scale of a high performance computing environment, such as the Summit supercomputer system.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A method, performed by a high-performance computing system, to enable mining of existing information and deriving new knowledge, the method comprising:

by the high-performance computer system, receiving, from multiple textual databases information about a set of articles and annotations relating to biomedical concepts that appear in the articles;

by the high-performance computing system, forming a first knowledge graph using the entire received information and annotations, the knowledge graph having nodes connected by edges, where the nodes include a set of article nodes representing respective biomedical articles, and a set of concept nodes representing respective biomedical concepts;

wherein edges between the concept nodes represent relations between biomedical concepts based on co-occurrence of biomedical terms in the articles,
wherein edges between the concept nodes and the article nodes represent relations between biomedical concepts and biomedical articles based on annotations or mentions within the biomedical articles, and
wherein edges between the article nodes represent relations between biomedical articles based on citation references;
by a set of processors of the high-performance computing system, determining shortest paths between all pairs of nodes of the first knowledge graph, the computing system performing the shortest-path computations by:
implementing a distributed Floyd-Warshall (FW) algorithm across multiple processing units in a two-dimensional process grid;
coordinating parallel updates using a message passing interface (MPI) that performs diagonal updates, panel updates, and MinPlus Outer Product computations over a tropical semiring executed by graphics processing units (GPUs);
performing computations in CPU-only mode, GPU-only mode, or CPU-GPU overlapping mode to optimize resource utilization based on workload;
performing asynchronous lookahead scheduling to overlap computation and communication; and
broadcasting matrix updates using a bandwidth-optimal ring communication protocol;
placing communicating processes based on optimal rank placement and performing intra-node communication optimization to reduce communication latency;
by the high-performance computing system, forming a second knowledge graph that includes the nodes of the first knowledge graph and the edges of the first knowledge graph that correspond only to the shortest paths;
by the high-performance computing system, further optimizing communication load by placing communicating processes on processing units that are physically proximal within the high-performance computing system; and
by the high-performance computing system, predicting yet-undiscovered biomedical relationships between the biomedical concepts based on the second knowledge graph, wherein the predictions are computed using the shortest paths as input features; and
outputting a ranked list of biomedical relationships based on the shortest-path computations to a display.

2. The method of claim 1, further comprises applying, while determining the shortest paths, a constraint to at least one of downweight, remove at least some edges along particular paths, and ignore a shortest path completely.

3. The method of claim 2, wherein the constraint represents a measure of relevance between concepts, between articles, or between concepts and articles.

4. The method of claim 1, wherein communications for determining the shortest paths is performed using only CPU communicators, only GPU communicators, or concurrently both CPU-GPU communicators of the high-performance computing system.

5. The method of claim 1, wherein the high-performance computing system uses GPU communicators when the distributed FW algorithm is performed only by GPUs.

6. The method of claim 5, further comprising reducing communication burden by instructing communicating sub-processes to run on resources of the high-performance computing system that are closer together.

* * * * *